United States Patent
Hofmann et al.

(10) Patent No.: US 10,977,866 B2
(45) Date of Patent: Apr. 13, 2021

(54) OUTPUT OF POSITION INFORMATION OF A MEDICAL INSTRUMENT

(71) Applicant: Siemens Healthcare GmbH, Erlangen (DE)

(72) Inventors: Bernd Hofmann, Erlangen (DE); Christian Ullrich, Nuremberg (DE); Harald Graupner, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/995,194

(22) Filed: Jun. 1, 2018

(65) Prior Publication Data

US 2018/0357825 A1    Dec. 13, 2018

(30) Foreign Application Priority Data

Jun. 9, 2017   (EP) ..................................... 17175269

(51) Int. Cl.
*G06T 19/00* (2011.01)
*A61B 90/00* (2016.01)
(Continued)

(52) U.S. Cl.
CPC ............ *G06T 19/006* (2013.01); *A61B 34/20* (2016.02); *A61B 34/76* (2016.02); *A61B 90/361* (2016.02);
(Continued)

(58) Field of Classification Search
None
See application file for complete search history.

(56) References Cited

U.S. PATENT DOCUMENTS

2004/0254454 A1* 12/2004 Kockro .................. A61B 90/36
                                                          600/424
2005/0015005 A1*  1/2005 Kockro .................. A61B 90/36
                                                          600/427
(Continued)

FOREIGN PATENT DOCUMENTS

WO    WO 2006075331 A2    7/2006
WO    WO 2006095027 A1    9/2006
WO    WO 2017066373 A1    4/2017

OTHER PUBLICATIONS

Kockro, Ralf, et al. "Dex-Ray: Augmented Reality Neurosurgical Navigation With a Handheld Video Probe." Neurosurgery, vol. 65, No. 4, 2009, pp. 1-24. (Year: 2009).*
(Continued)

*Primary Examiner* — Peter Hoang
(74) *Attorney, Agent, or Firm* — Harness, Dickey & Pierce, P.L.C.

(57) ABSTRACT

A method is for output of position information of a medical instrument, configured to penetrate at least partly an area of the body of a patient. A structure image, an instrument image and an operation scene image are registered with one another. A registered structure image, a registered instrument image and a registered operation scene image are produced from the registration. An overlay image is displayed with a VR or AR display facility, including at least parts of the registered structure image of the registered operation scene image (BrO)—or the real view of the corresponding part of the real area of the body—and of the registered instrument image. A corresponding image generation system is also disclosed.

26 Claims, 6 Drawing Sheets

(51) Int. Cl.
    *A61B 34/20*     (2016.01)
    *A61B 34/00*     (2016.01)
    *G06F 3/01*     (2006.01)
    *A61B 90/50*     (2016.01)
    *H04N 7/18*     (2006.01)

(52) U.S. Cl.
CPC .............. *A61B 90/37* (2016.02); *G06F 3/016* (2013.01); *G06T 19/003* (2013.01); *A61B 2034/2057* (2016.02); *A61B 2034/2065* (2016.02); *A61B 2090/364* (2016.02); *A61B 2090/365* (2016.02); *A61B 2090/371* (2016.02); *A61B 2090/373* (2016.02); *A61B 2090/502* (2016.02); *G06T 2200/08* (2013.01); *G06T 2210/41* (2013.01); *H04N 7/181* (2013.01)

(56) References Cited

U.S. PATENT DOCUMENTS

2006/0293557 A1* 12/2006 Chuanggui ............ A61B 90/36
    600/101
2015/0185846 A1* 7/2015 Otto ........................ G06F 3/016
    345/156

OTHER PUBLICATIONS

Extended European Search Report #17175269.4 dated Nov. 21, 2017.
Office Action for European Patent Application No. 17175269.4 dated Nov. 19, 2019.
Office Action for European Patent Application No. 17175269.4 dated Nov. 19, 2019 and English translation thereof.

* cited by examiner

FIG 1  State of the Art

OUTPUT OF POSITION INFORMATION OF A MEDICAL INSTRUMENT

PRIORITY STATEMENT

The present application hereby claims priority under 35 U.S.C. § 119 to European patent application number EP 17175269.4 filed Jun. 9, 2017, the entire contents of which are hereby incorporated herein by reference.

FIELD

At least one embodiment of the invention generally relates to a method and to an image generation system for output of position information of a medical instrument, which is penetrating at least partly into an area of a patient's body, in particular for displaying a multi-sensor presentation of this body area.

BACKGROUND

The penetrations of a human body with medical devices, such as endoscopes, for example a puncturing of cavities within a skull with such an endoscope, is a widely-used method for diagnostics and therapy of various diseases in medicine. In this case the medical instrument is introduced initially through a small opening into the body. In the puncturing of the ventricle system for example the instrument is introduced through a small opening in the skull cap, wherein as a rule healthy brain tissue must be pierced with the instrument in order to arrive at the destination location. In such cases the instrument must be maneuvered to said location past structures that are necessary for life. For these reasons such an intervention is associated with a high risk of complications that are the result of injury to tissue, e.g. brain tissue or vessels, and can possibly be associated with internal bleeding or with neurological deficiency symptoms.

A method that is still widely used, in particular when setting up a so-called ventricular drainage for example, is blind puncturing. In this method the destination location is reached without visual control and is based only on the experience of the operator. Therefore a number of attempts are often necessary before the destination is reached. This is naturally associated with a higher risk of the occurrence of injuries and complications, in the worst cases it is linked to neurological deficiency symptoms and a delayed recovery.

A further development of the puncturing technique resides in the use of navigation methods (neuronavigation), which allows the path of the instrument in the skull to be followed at least indirectly on a display. A disadvantage of such a presentation is the difficulty in guiding the instrument by the operator, since, for reasons of sterility, the display can mostly not be set up in a line with the direction of guidance of the instrument and the operator thus either constantly has to switch their attention between instrument and display or must adopt an unfavorable posture. This all leads, even here—despite navigation methods—to the destination frequently not being reached in the first puncturing attempt and thus to the risk of complications likewise increasing.

SUMMARY

At least one embodiment of the present invention provides a safe and convenient method and a corresponding image generation system for presentation of an area of the body, with which at least one of the disadvantages mentioned above are avoided.

At least one embodiment of the present invention is directed to a method and at least one embodiment of the present invention is directed to an image generation system.

At least one embodiment of the present invention is directed to a method, used for output of position information of a medical instrument, in particular an endoscope, wherein the medical instrument penetrates at least partly an area of the body of a patient. "Patients" within the framework of this invention can basically be all possible living beings, human or animal, but can also be inanimate objects, such as mummies for example.

At least one embodiment of the present invention is directed to an automated method of presenting images or an image generation system explained in greater detail below, which makes such presentations possible. Even if at least one embodiment of the invention can in particular support an operator within the framework of an intervention, it does not relate to the intervention or to the operations per se.

At least one embodiment of the present invention is directed to a method, which is suitable in particular as an alternative or in addition to multi-sensor presentation of an area of the body before and/or during the penetration by a medical instrument, comprises a number of steps, which will be explained in greater detail below.

At least one embodiment of the present invention is directed to a A method for output of position information of a medical instrument, which at least partly penetrates an area of the body of a patient, comprising:

a) Provision
   of a structure image comprising internal structures of the area of the body and
   of an instrument image comprising at least the part of the medical instrument used for the operation, b) Creation of an operation scene image comprising at least a surface of the area of the body concerned together with the operating medical instrument, c) Registration of at least areas of the operation scene image, of the structure image and of the instrument image with one another, wherein at least the structure image and the corresponding area of the body in the operation scene image and also the instrument image with the medical instrument in the operation scene image are registered with one another, d) Display of an overlay image with a VR or AR display facility
   wherein the overlay image comprises at least a part of the registered structure image in the form of an overlay with the registered operation scene image or the real view of the corresponding part of the real area of the body and comprises at least a part of the registered instrument image in that area in which the medical instrument is covered in the registered operation scene image by the surface of the area of the body,
   and/or
   wherein the overlay image comprises the operation scene image, the registered operation scene image or the real view of the corresponding part of the real area of the body together with a presentation of navigation data for the penetration.

At least one embodiment of the present invention is directed to an image generation system for output of position information of a medical instrument, which at least partly penetrates an area of the body of a patient, comprising A structure image interface for provision of a structure image comprising internal structures of the area of the body, An instrument image interface for provision of an instrument image comprising at least a part of the medical instrument, A recording unit for creating an operation scene image comprising at least a surface of the area of the body concerned together with the medical instrument, A registration unit for registration of at least areas of the operation scene image, of the structure image and of the instrument image with one another, wherein at least the structure image and the corresponding area of the body in the operation scene image as well as the instrument image with the medical instrument in the operation scene image are registered with one another, An interface for a VR or AR display facility, which is embodied to display an overlay image, i) wherein the overlay image comprises at least a part of the registered structure image in the form of an overlay with the registered operation scene image or the real view of the corresponding part of the real area of the body and comprises at least one part of the registered instrument image in that area, in which the medical instrument in the registered operation scene image is hidden by the surface of the area of the body and/or ii) wherein the overlay image comprises the operation scene image, the registered operation scene image or the real view of the corresponding part of the real area of the body together with a presentation of navigation data for the penetration.

A large part of the previously mentioned components of the image generation system, in particular the interfaces and/or the registration unit, can be realized entirely or in part in the form of software modules in a processor of a corresponding control device. A largely software-based realization has the advantage that even facilities already used previously can be integrated into the system in a simple manner by a software update, in order to work in an inventive way of at least one embodiment. To this extent, at least one embodiment is directed to a corresponding non-transitory computer program product with a computer program, which is able to be loaded directly into a memory device of a computing device of the image generation system, with program sections for carrying out all steps of an embodiment of the inventive method when the program is executed in the computing device. Such a non-transitory computer program product, as well as the computer program, may possibly comprise additional elements such as e.g. documentation and/or additional components, also hardware components, such as e.g. hardware keys (dongles etc.) for using the software.

At least one embodiment is directed to a non-transitory computer-readable medium, for example a memory stick, a hard disk or another transportable or permanently-installed data medium, can be used for transport to the computing device and/or for storage on or in the computing device, on which the program sections of the computer program able to be read in and executed by a computing unit of the computing device are stored. For this purpose the computing unit can have one or more interoperating microprocessors or the like for example.

BRIEF DESCRIPTION OF THE DRAWINGS

The invention will be explained below once again in greater detail with reference to the enclosed figures on the basis of example embodiments. In this explanation the same components are provided with identical reference characters in different figures. The figures are as a rule not true-to-scale. In the figures.

DETAILED DESCRIPTION OF THE EXAMPLE EMBODIMENTS

Figure 1:
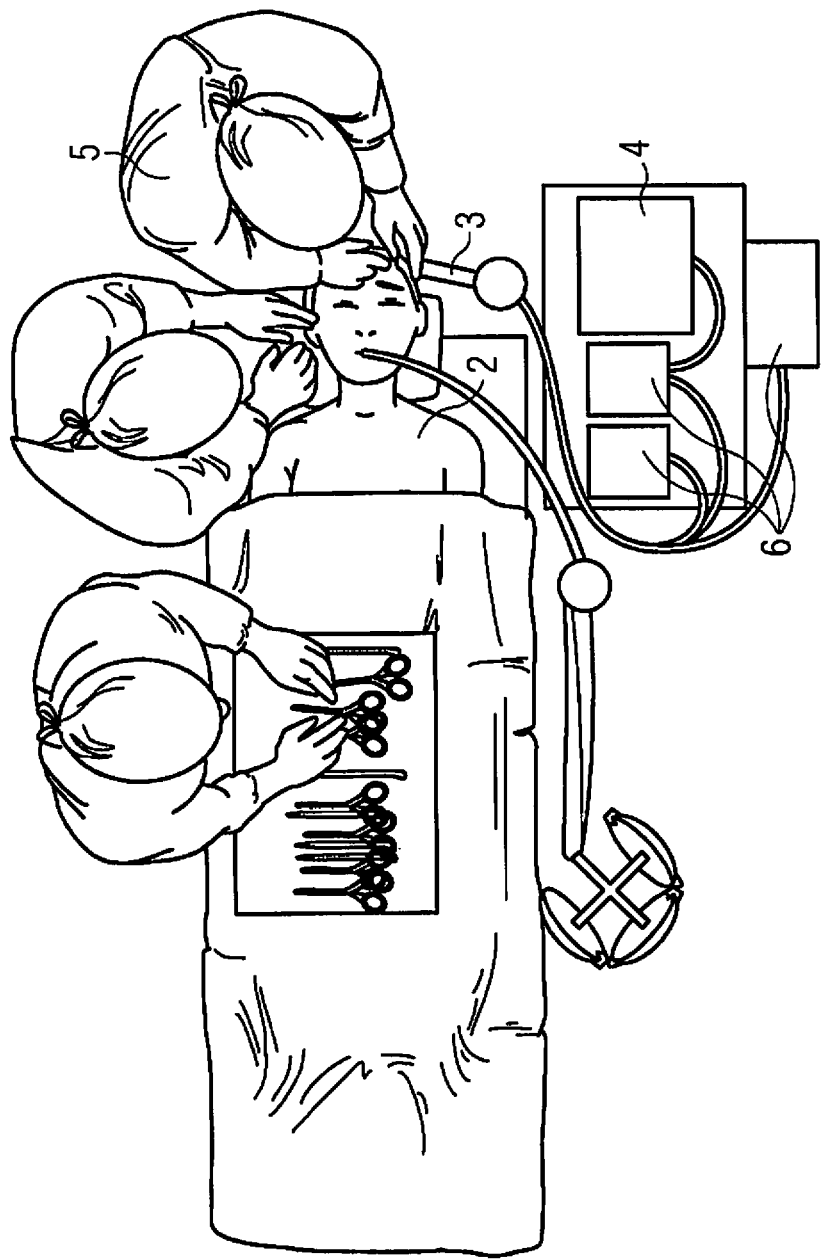
FIG. 1 shows a diagram of a head operation according to the current prior art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the present invention, a method firstly includes a provision, e.g. a creation, of a structure image and of an instrument image. To this end, one of these images or both images are preferably 3D presentations. This can be done for example by a provision of multidimensional image data, e.g. of CT images, which contain a recording of the interior of the area of the body involved. The term "multidimensional" in this case means three space dimensions or, possibly together with the time, four dimensions, wherein the multidimensional image data can also be given in the form of a stack or a series of two-dimensional images. The area of the body in this case can be the head or the chest cavity for example.

The structure image in this case comprises internal structures of the area of the body concerned. These structures can be obtained by a recording made previously, e.g. the aforementioned CT images, but they can also be made directly during the medical intervention. In particular the image data can be prepared for the structure image, e.g. a removal of noise or a recognition or marking of different structures in the image.

The instrument image comprises at least the part of the medical instrument used for the operation or its image data, which in particular can be stored in a database as a three-dimensional presentation, e.g. a CAD presentation. All elements that are introduced for the operation into the area of the body, such as e.g. endoscopes and catheters, are seen as an instrument. Furthermore consumables such as e.g. ventricular catheters are medical instruments in the sense of the invention.

In addition an operation scene image is produced, for example by a direct recording and/or a (part) reconstruction. This operation scene image contains image data comprising at least one surface of the area of the body involved together with the operating medical instrument, i.e. for an intervention in the brain, an external image of at least a part of the head at which the instrument penetrates into the head. It is sensible to produce this operation scene image during the operation and to update it constantly, in order to always show the current operation scene. The operation scene image shows the surface of the area of the body, such as e.g. the head of a patient. As a rule this shows the surface of the body, but, with an opened-up area of the body, it can also show the surface of structures actually lying inside this area.

Basically a camera image of the area of the body together with information about the real relative position and orientation of the area of the body and of the medical instrument in space is sufficient for the operation scene image. Preferably the operation scene image comprises 3D data of the patient, in particular, when it is recorded by cameras installed in the room, since depending on the angle of view of the operator, an individually suitable view is to be created.

Based on the aforementioned images there is at least in some areas an automatic registration of the operation scene image, of the structure image and of the instrument image with one another, wherein at least the structure image and the corresponding area of the body in the operation scene image and also the instrument image with the medical instrument are registered with one another in the operation scene image. In this case it is basically irrelevant which of these images serves as reference image for the registration, to which the image or the other images will be adapted (registered to these) and which are the object images, which are adapted to the reference image. Each image can also be adapted, within the framework of the registration, to a common standard. However in many cases it is best to use the operation scene image as reference image during the registration, since this makes the later presentation easier.

Essentially it is only important during the registration for the structure image and the instrument image to fit into the operation scene image after the registration with the corresponding size, the corresponding position and the corresponding orientation. Even if one of the images is not to be changed during the registration, for a better understanding, this text will still refer after the registration to a registered structure image, a registered instrument image and a registered operation scene image, which are produced by the registration. In other words, the structure image, the instrument image and the operation scene image become the registered structure image, registered instrument image and registered operation scene image, in that they have passed through the registration process.

The registered instrument image corresponds to the instrument of the registered operation scene image or vice versa. The registered structure scene image would correctly reproduce the internal structure of the area of the body, if this were to be transparent in the registered operation scene image.

Before or with the registration there can be the acquisition of the position and orientation of the corresponding real area of the body relative to the operator or an acquisition of the position and orientation of the real medical instrument relative to the operator, e.g. by evaluation of the operation scene image, provided this is available as a 3D image or has at least been created from a recording of two cameras. This has the advantage that a simpler and/or more precise registration of the structure image or of the instrument image can be achieved.

In the event that the overlay image is to be shown from the view of the present operator, e.g. as an Augmented Reality display with a real operation scene, it is necessary where possible to adjust the operation scene image accordingly. In the event of the operation scene image having been recorded, e.g. by cameras on the display facility, directly from the angle of view of the operator, as a rule no additional effort must be made. In the event of the operation scene image having been recorded by fixed or movably installed room cameras, the angle of view and the position of the operator, or of their display facility, should be determined, in order to adapt the operation scene image accordingly. In cases in which the operation scene image is formed both by recordings from cameras on the display facility at the operator (e.g. by cameras installed in AR headset) and also from recordings from room cameras, these different recordings must be coordinated or registered with one another.

After the registration an overlay image is displayed with a VR or AR display facility (VR: Virtual Reality or AR: Augmented Reality).

This overlay image comprises at least a part of the registered structure image in the form of a (registered) overlay with the registered operation scene image or the real view of the corresponding part of the real area of the body and of the registered instrument image at least in that region in which the medical instrument is covered in the registered operation scene image by the surface of the area of the body. Thus, in the overlay image, the corresponding parts of the registered structure image are located where the corresponding structures can also be found in the registered operation scene image. In exactly the same way at least the part of the registered instrument image is to be found where the medical instrument would be seen, were it not to be located in the area of the body. Through the overlay image the impression will thus be created of being able to look into the area of the body. This could also be referred to by the term "Mixed Reality" (MR).

As an alternative or in addition the overlay image can comprise the operation scene image, the registered operation scene image or the real view of the corresponding part of the real area of the body together with a presentation of navigation data for the penetration. The overlay image can thus contain markings for the insertion point for the penetration, the path to the destination region or direction information.

In an example in which a ventricular puncturing is to take place and the medical instrument is an endoscope and the area of the body is a human skull, the overlay image as a (registered) structure image could comprise an MRT or CT recording of the brain area with the ventricle, which has been prepared and registered with the view of the skull. The operator would be offered a presentation by the display facility, in which he can always see the tip of the endoscope in the head, since this is shown to him by the registered instrument image. In addition the operator can always recognize the brain and/or the ventricle, since this is mapped by the registered structure image where it would also be located when looking at the skull of the patient.

Even if the structure image—as stated above—is preferably a 3D image, it can in principle also be a two-dimensional image, if it is insured that it lies in the plane of the (registered) operation scene image. It is preferred that the registered structure image is a two-dimensional image, which may possibly have been created from a 3D image, since this reduces the computing overhead in the presentation.

As a rule, as mentioned, many current operation scene images in each case are recorded after one another, or the method is run through multiple times, since the angle of view of the operator or the position of the medical instrument constantly changes in practice. This enables an overlay image to be created, which always has the current situation in the operation as its basis.

Preferably the possibility of zooming is available to the operator. To do this, after an operator command the overlay image presented with all its components, i.e. the registered operation scene image, the registered structure image and the registered instrument image is enlarged or reduced.

At least one embodiment of the inventive image generation system for output of position information from a medical instrument, which at least partly penetrates an area of the body of a patient, is in particular designed to carry out the aforementioned method and comprises at least the following components:

A structure image interface, which can possibly also be referred to as an "image creation unit", to provide a structure image, which comprises internal structures of the area of the body. This structure image interface is preferably an interface, which can receive image data of a medical facility, e.g. of a Computed Tomograph (CT). To this end it is designed in particular to accept data in accordance with the DICOM standard (DICOM: "Digital Imaging and Communications in Medicine"). Preferably the structure image interface is also designed to adapt the image data for an embodiment of the inventive image generation system by automatically undertaking a conversion into the required format for example.

An instrument image interface for provision of an instrument image comprising at least one part of the medical instrument. The instrument image interface is preferably designed to access a database with instrument images and to accept image data, in particular 3D data such as e.g. CAD data and to make this available to the image generation system.

A recording unit, e.g. a camera arrangement, for creation of an operation scene image comprising the area of the body involved together with the medical instrument. In this case the recording unit is preferably designed for recording image data and especially preferably also for processing the same.

A registration unit for registering at least some areas of the operation scene image, of the structure image and of the instrument image with one another, wherein at least the structure image and the corresponding area of the body in the operation scene image as well as the instrument image are registered with one another with the medical instrument in the operation scene image. This registration unit thus makes possible the generation of a registered structure image and of a registered operation scene image and also of a registered instrument image via registration of the structure image with the corresponding area of the body in the operation scene image and of the instrument image with the medical instrument in the operation scene image. Preferably the registration is done in a form such as has already been described above as part of the method. In this process the recorded images can be worked with directly or computed images can be worked with, such as e.g. in the event of room cameras recording the operation scene image and of this being changed so that it correctly reproduces the angle of view of the operator onto the scene.

An interface for a VR or AR display facility, which is embodied for displaying an overlay image. Depending on the design of the image generation system, the VR or AR display facility can also be comprised by the image generation system. The said interface in this case is designed so that the overlay image, which is output for the VR or AR display facility, comprises at least a part of the registered structure image as well as the registered instrument image. The registered structure image is available in this case in the form of an overlay with the corresponding area of the body in the registered operation scene image or the real view of the corresponding real area of the body. The registered instrument image shows at least that region in which the medical instrument is hidden in the registered operation scene image by the surface of the area of the body.

As an alternative or in addition thereto the overlay image, which is output for the VR or AR display facility, comprises an overlay of a presentation of navigation data with the operation scene image, the registered operation scene image or with the real view of the corresponding (real) area of the body.

At least one embodiment of the present invention thus makes possible an output of position information about the position of the medical instrument in the form of an advantageous conjunction between imaging, automated image processing and detection and also Augmented Reality or Virtual Reality, so that the operator in effect "sees" where he is currently moving with his instrument in the structure of the area of the body.

A large part of the previously mentioned components of the image generation system, in particular the interfaces and/or the registration unit, can be realized entirely or in part in the form of software modules in a processor of a corresponding control device. A largely software-based realization has the advantage that even facilities already used previously can be integrated into the system in a simple manner by a software update, in order to work in an inventive way of at least one embodiment. To this extent, at least one embodiment is directed to a corresponding non-transitory computer program product with a computer program, which is able to be loaded directly into a memory device of a computing device of the image generation system, with program sections for carrying out all steps of an embodiment of the inventive method when the program is executed in the computing device. Such a non-transitory computer program product, as well as the computer program, may possibly comprise additional elements such as e.g. documentation and/or additional components, also hardware components, such as e.g. hardware keys (dongles etc.) for using the software.

At least one embodiment is directed to a non-transitory computer-readable medium, for example a memory stick, a hard disk or another transportable or permanently-installed data medium, can be used for transport to the computing device and/or for storage on or in the computing device, on which the program sections of the computer program able to be read in and executed by a computing unit of the computing device are stored. For this purpose the computing unit can have one or more interoperating microprocessors or the like for example.

Further, especially advantageous embodiments and developments of the invention emerge from the dependent claims as well as the description given below. In this case, an embodiment of the inventive method or an embodiment of the inventive image generation system can also be developed analogously to the dependent method claims or parts of the description. In particular individual features of different example embodiments or variants can also be combined into new example embodiments of variants.

It is preferred in relation to the overlay image that those parts of the medical instrument that are visible in the operation scene image are presented as a real map or as image data of the operation scene image, i.e. not as a part of the (registered) instrument image in the overlay image, preferably as from the transition from visible to the part located in the area of the body. Thereby only that part of the instrument image that is not visible in the operation scene image is presented as "virtual", which improves the presentation for the operator. Through at least one embodiment of the inventive registration described above it is insured in this case that the virtual image of the instrument is displayed exactly at the position at which the corresponding part of the real instrument is also located.

It is especially preferred that the registered part of the instrument image is graphically highlighted, in particular the regions that are not to be seen in the operation scene image by the instrument, for example by a more intense or modified coloring. This has the advantage that the covered regions of the instrument can be better perceived as such.

Preferably regions of the area of the body traversed, e.g. tissue already traversed in the overlay image by the medical instrument, are hidden in the presentation of the registered structure image or their transparency is increased. This has the advantage that the focus of the operator is directed to the relevant regions and to structures still to be passed. Technically this can be realized for example, in a 3D presentation of the structure image, by all those regions being hidden that lie outside a freely-definable radius around the destination structure. The radius should in this case not be less than the distance of the tip of the instrument from the destination structure, i.e. both structures must be visible in the mixed reality. This distance can be established for example during the registration, since the destination structure is known in the structure image, as is the location of (registered) structure image and (registered) instrument image.

It is especially preferred for specific, defined structures in the structure image to be segmented and to be present as separate image or data objects. Preferably for example specifically identified structures cannot be hidden or structures hidden object-by-object. In this way veins can continue to remain visible for example, although the medical instrument has already passed them, while other body tissue is hidden.

Preferably, for navigation based on the structure image, the destination structure of the penetration is established. This can occur manually, however it is preferable for an automatic recognition of the relevant target structures to be carried out, e.g. with algorithms for machine learning. This destination structure and/or the path to it will then be marked in the overlay image, in particular in the registered structure image, or spatially simulated for the operator in the overlay image.

In the event of the medical instrument having a tip, it is preferred that the respective current position of the tip of the medical instrument be recognized automatically and marked in the overlay image. Preferably this occurs in the (registered) instrument image, e.g. with the assistance of the 3D dataset and navigation software and/or of simulation results.

It is likewise preferable for auxiliary information, in particular navigation information, e.g. arrows, direction specifications, distances etc., to be incorporated into the overlay image, which make it easier to reach the destination structure during the penetration. Preferably this auxiliary information shows the respective direction in which the tip of the instrument must be guided to the destination structure. This makes it easier for the operator to reach the destination during the operation. The auxiliary information can be two-dimensional presentations, but depending on the application three-dimensional presentations are preferred.

Preferably specific relevant, in particular safety-relevant, structures of the area of the body are specially marked in the registered structure image. Such a marking can be done manually beforehand or after an automatic recognition via artificial intelligence in an automatic way. In this case it is preferred that these relevant structures are incorporated color-coded by the display facility into the overlay image.

As an alternative or in addition thereto it is preferred that possible collisions of the medical instrument, in particular its tip, with these relevant structures are recognized automatically and a warning signal is output. Such a warning signal can be of an acoustic, visual or haptic nature. This helps to avoid complications, e.g. bleeding on injury to vessels.

Preferably the destination structure or its position is marked temporarily in the overlay image, if said structure has left the field of view of the display facility and/or comes back into the field of view. Preferably the destination structure, in the event of it having temporarily left the field of view and then having come back into the image, can be temporarily specially marked in the overlay image. Such a marking can in particular be made in color or by enlargement and has the advantage of making it easier to find again. Preferably this temporary marking is done for a short time, wherein it preferably remains in existence for no longer than 5 seconds, in particular no longer than 1 second. This prevents the operator from becoming tired, making it easier for them to find smaller destination structures, and can thereby shorten the duration of the operation. For optically similar structures it also helps to safely recognize the relevant destination structure again, and thus likewise increases the safety during the operation. As an alternative or in addition a marking of the destination structure that is currently no longer located in the field of view, can be shown by an indicator, for example an arrow or the like, which indicates in the field of view the direction in which the destination structure is located next to the field of view.

Preferably the image generation system comprises forced feedback generators, which make a haptic feedback possible and which in particular are arranged on or in the medical instrument. A haptic feedback in this case comprises a force for example, which acts against the movement of the medical element, a vibration, or a heating. Preferred forced feedback generators are vibrators, thermoelements or force transmitters.

It is preferred that these forced feedback generators support the guidance of the medical instrument in a haptic way and/or emit a haptic warning if there is a threat of damage to internal structures of the area of the body. This is preferably done by modifying the haptics of the medical instrument. In particular in this case the virtual resistance of relevant structures is transmitted by sensors to the operator and the latter can decide the extent to which he takes account of the accidental displacement of e.g. blood vessels. The shear stress analysis of these structures can be helpful in the generation of the feedback information in this case, which is done by corresponding software. Preferably a haptic impression is achieved by way of vibration elements or the like.

Preferably a monitoring of a deviation of the spatial course of the part of the medical instrument located in the area of the body from a predetermined course is undertaken. Especially preferably a warning signal is output if a maximum permitted deviation is exceeded. Such a warning signal can have haptic and/or acoustic and/or optical components. This is in particular of advantage when the operator is only focusing on the tip of the instrument and the target region and in this case the course of the part of the instrument remote from the tip varies greatly. These deviations from the original path can likewise lead to injuries to relevant structures and should be avoided. Thus safety can likewise be considerably enhanced during the operation.

It is preferred that, via control mechanisms, parts of virtual mapping data and/or additional information are incorporated into or hidden in the overlay image and/or the function of devices, in particular of medical devices, is controlled. Such control mechanisms can be foot switches for example, or so-called "intelligent" control mechanisms, such as e.g. voice control, and/or buttons in the overlay image.

For example an endoscope image or live image generated by the endoscope can be shown or hidden during a video endoscopy or disruptive information can be hidden. The latter is helpful for not seeing the destination structures to be handled "covered over" by virtual information, which would lead to small structures that are to be handled being recognized less well.

It is preferred that an endoscope image is additionally contained in the overlay image, which in particular, e.g. as mentioned above, can be shown and hidden in a controlled manner. This endoscope image can preferably be fixed virtually at a position in the overlay image or in the space within the overlay image. This can be done in a preferred manner at the position of the endoscope tip of the registered instrument image or at the focus point of the endoscope optics. This produces the advantageous option of also carrying out the endoscopic intervention carried out via the display facility, independently of a further monitor. This enhances the safety of the intervention, since the operator also always has the extracorporeal "axis" of his instrument in his field of view, which results in a more stable manual guidance of the instrument and thus reduces the complication rate and speeds up the intervention. With three-dimensional video endoscopy the body's own structures are preferably likewise presented as three-dimensional structures. The image signal of the endoscope is tapped of in this case at suitable interfaces, e.g. HDMI, and transferred by information technology algorithms into the overlay image. The position of the endoscope camera, or of the camera optics and of the structures in the live image can be established with reference to the calculated coordinates in the reference system.

In the preferred case of the operator having the option of a zoom, it is especially preferred that with a preset level of enlargement of the overlay image, the endoscope image is shown at the position of the endoscope tip, preferably at a size in which the structures shown in the endoscope image have the size and position of the corresponding structures of the registered structure image. It is especially preferred for the endoscope image to be registered with the structure image.

Preferably the operation scene image comprises information about the position and orientation of the area of the body and of the medical instrument in the room. It is preferably created from images that are recorded via cameras, wherein the cameras involved are preferably integrated in the display facility and/or positioned in the room. A combination of the two camera arrangements is especially preferred in this case.

The cameras can be installed fixed in the room in this case, but can also be mobile, such as e.g. attached to the display facility of the operator, or be movable in the room in another way. It is of advantage with room cameras, which are not moved automatically with the head of the operator, if they no longer change their position after an initial setting in the room. If despite this a position change in the room takes place, it is of advantage for the room to have fixed structures in the region of the recorded operation scene, e.g. a marker on the operating table, so that an assignment of the operation scene in the room is possible, in particular relative to the operator and their direction of view. In this regard it is preferable for the display facility of the operator to be designed so that its position and orientation in the room can be established on the operation scene images.

Preferably, for creation of the operation scene image, in particular for establishing the position and orientation of the area of the body and of the instrument in the room, information from other imaging systems or 3D sensors is used additionally. Such systems or sensors can be accelerometers, transmitters or receivers for location information for example.

When the method is carried out, as described above, the destination structure, e.g. a puncturing or the surface contour of the patient is preferably identified first of all in a sectional image dataset. In this case an automated identification is employed in particular, in which the operator merely marks the destination structure in one or in a few sectional images. The surface of the patient is preferably recognized automatically in this case.

The registration of virtual destination and surface of the patient (also known as "coregistration") then preferably takes place. Here the registration of the patient in particular takes place via cameras, which are set up in the room, or in an optimum way with the aid of cameras that are integrated in the AR headset. The latter offers the advantage that the effort of reprojection is minimized, because the view of the user no longer has to be additionally extrapolated from the reference system.

To increase the detailing and precision, information from other imaging systems or 3D sensors can also be used. Preferred imaging systems or 3D sensors could already be being used for collision detection within the imaging system or their coordinate systems or three-dimensional image data could be used. This information can likewise be used for a registration. This method offers the advantage that the effort of reprojection is minimized, because the view of the user no longer has to be extrapolated in addition from the reference system. To this end the recorded images are used, in order by stereoscopic reprojection to deduce the physical dimensions of the patient and of the room surrounding him.

Thus an additionally attached reference marking can make orientation possible even for a patient with a sterile covering, for registration in coordinate systems of different systems this reference marking can possibly also be dispensed with.

Overall the virtual surface of the patient is thus automatically registered with the real surface and thus the lesion is also virtually mapped "in the body" of the patient. This can then be presented to the operator in the headset display.

As described above, the medical instrument, which is used for the operation—e.g. for puncturing—is also registered in the virtual room and transferred into a virtual map, which is overlaid with the real instrument, at least the non-visible part. On penetration of the instrument into the body of the patient the real image of the instrument is then no longer displayed, but the virtual image will be mapped partially, i.e. at least as from the transition from the visible part to the part located in the body, for the operator. It is thus possible for the operator, in a convenient posture always to have the patient in view and to advance the instrument to the destination in the optimum working position in a targeted manner and with only slight corrections and on the basis of the virtual image. It is to be expected that thus a successful intervention, e.g. a puncturing, in particular of small structures, occurs at the first attempt and the risk of complications is greatly reduced.

These advantages, as well as resulting in a lessening of the complication quotas, also result in a reduction in the operation time, which overall is not only good for the patient, but also achieves a reduction in the load on the health system.

Moreover, under some circumstances in a few cases even the carrying out of a post-operative control imaging can be omitted, which can lead to a reduction in the radiation load on the patient and to a cost reduction.

FIG. 1 shows a diagram of a head operation, e.g. the puncturing of a ventricle, according to the current prior art. A patient 2 lies on a couch and is operated on by an operator 5 with a medical instrument 3, e.g. an endoscope. On a display 4 he can see a video image, which is recorded by a camera, which is located in the tip of the medical instrument 3. An instrument assistance system 6 supports the function/navigation of the medical instrument 3.

The disadvantage of this arrangement is that the operator 5 constantly has to turn his head in order to look at the display 4. During this movement the location of the medical instrument 3 in the head of the patient 2 can change slightly, so that the operator 5 can see an image which does not appear as it is during his operation activity, or that after looking at an image and movement of the head, the tip of the medical instrument 3 is no longer located in the position at which the image being looked at has been recorded. Furthermore unintentional movements can result in injuries to relevant structures.

Figure 2:
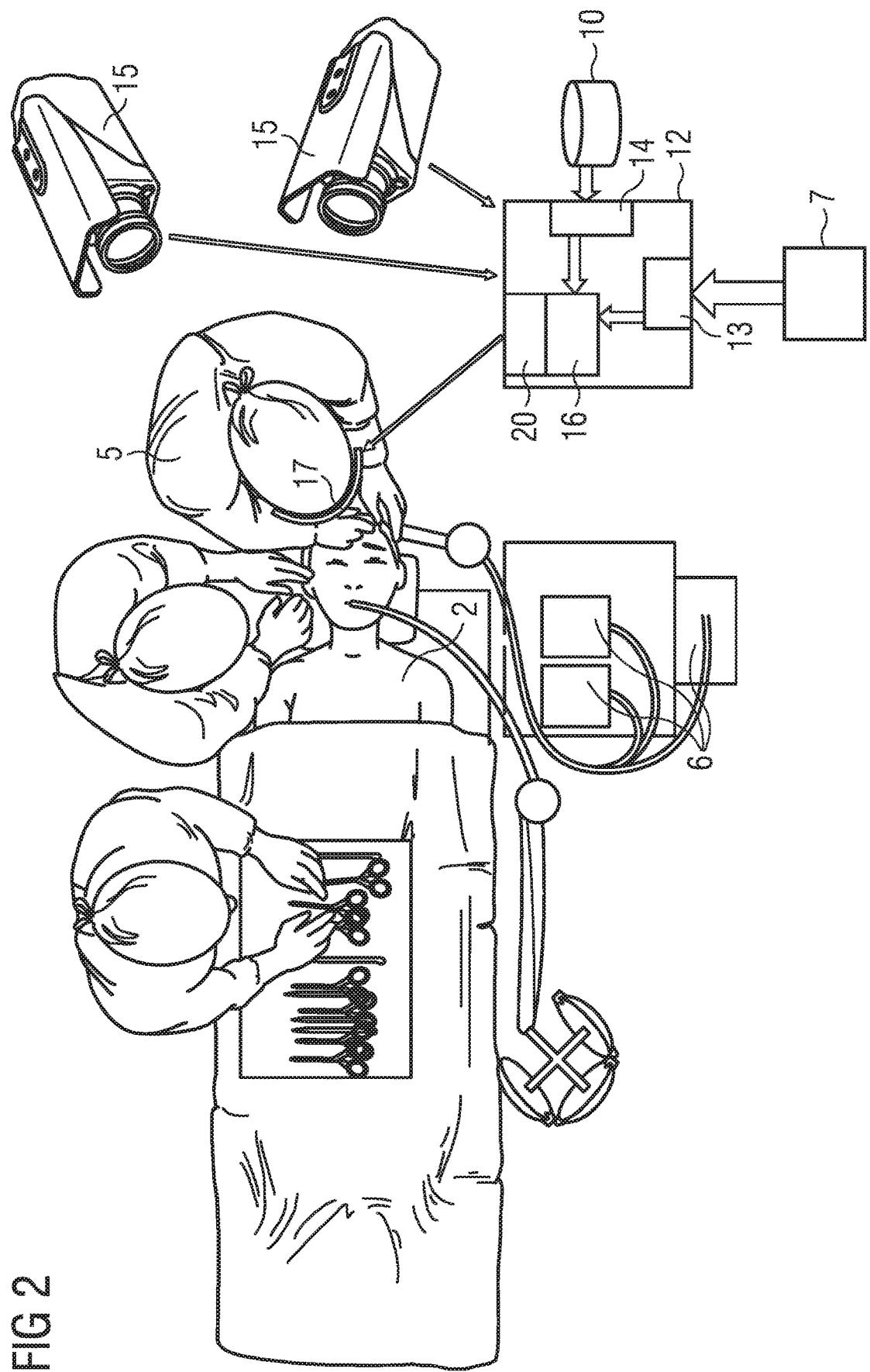
FIG. 2 shows a diagram of a head operation with support by a preferred form of embodiment of an inventive image generation system.

FIG. 2 shows a diagram of a head operation with support by a preferred form of embodiment of an inventive image generation system 12. Here too a patient 2 is having their head operated on by an operator 5 via a medical instrument 3. Unlike in FIG. 1 however, the operator 5 no longer has to look at a display 4, but wears an AR headset 17 as AR display facility 17 of an overlay image BU, as is shown for example in FIG. 4.

This overlay image UB is created by the image generation system 12 and sent via the interface 20 to the AR headset 17. This can be done by a cable connection, but also wirelessly, e.g. via WLAN or Bluetooth.

The image generation system 12 comprises a structure image interface 13, which can receive image data generated by a computed tomograph 7 or another medical imaging system, such as a magnetic resonance tomograph—from inside the head 1 of the patient 2. This image data has been prepared in advance and comprises a structure image BS, as is shown for example in FIG. 5. In the structure image BS the ventricle 22 to be punctured can be seen as the destination structure and blood vessels 21 which represent safety-relevant structures can also be seen. Before the operation the image generation system 12 has received the structure image BS.

The image generation system 12 furthermore comprises an instrument image interface 14, which can receive CAD image data from a database 10. This CAD image data has been prepared in advance in a CAD program in accordance with the dimensions of the real medical instrument 3 and represents the instrument image BIn, as is likewise shown in FIG. 5 for example. The tip of the endoscope, which can be pushed into the head of the patient, is shown in particular in the instrument image BIn. Before the operation the image generation system 12 has received the instrument image.

Figure 5:
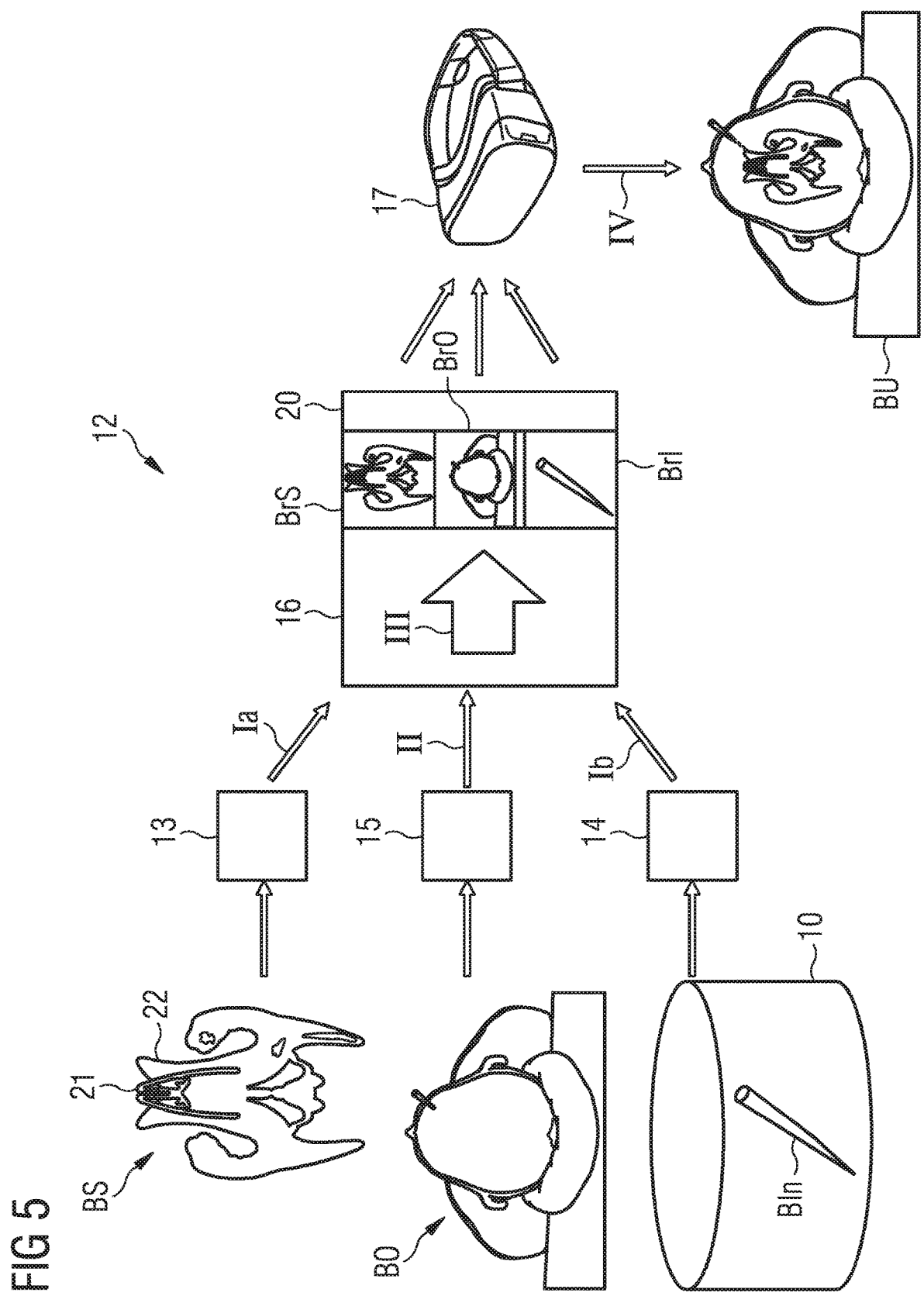
FIG. 5 shows a diagram of the course of a preferred form of embodiment of an inventive method.

Two cameras 15 serve as recording units for the operation scene image BO, as is likewise shown in FIG. 5, and make their recorded image data available to the image generation system 12. The cameras 15 are shown here in the room, but they can also be cameras 15 that are integrated into the AR headset 17. More than two cameras can also be used. As an alternative or in addition a stereo camera or the like could also be employed.

A registration unit 16 carries out an image registration of the structure image BS, of the instrument image BIn and of the operation scene image BO with one another and generates a registered structure image BrS, a registered instrument image BrI and a registered operation scene image BrO. This process will be described in greater detail below within the framework of FIG. 5.

Figure 3:
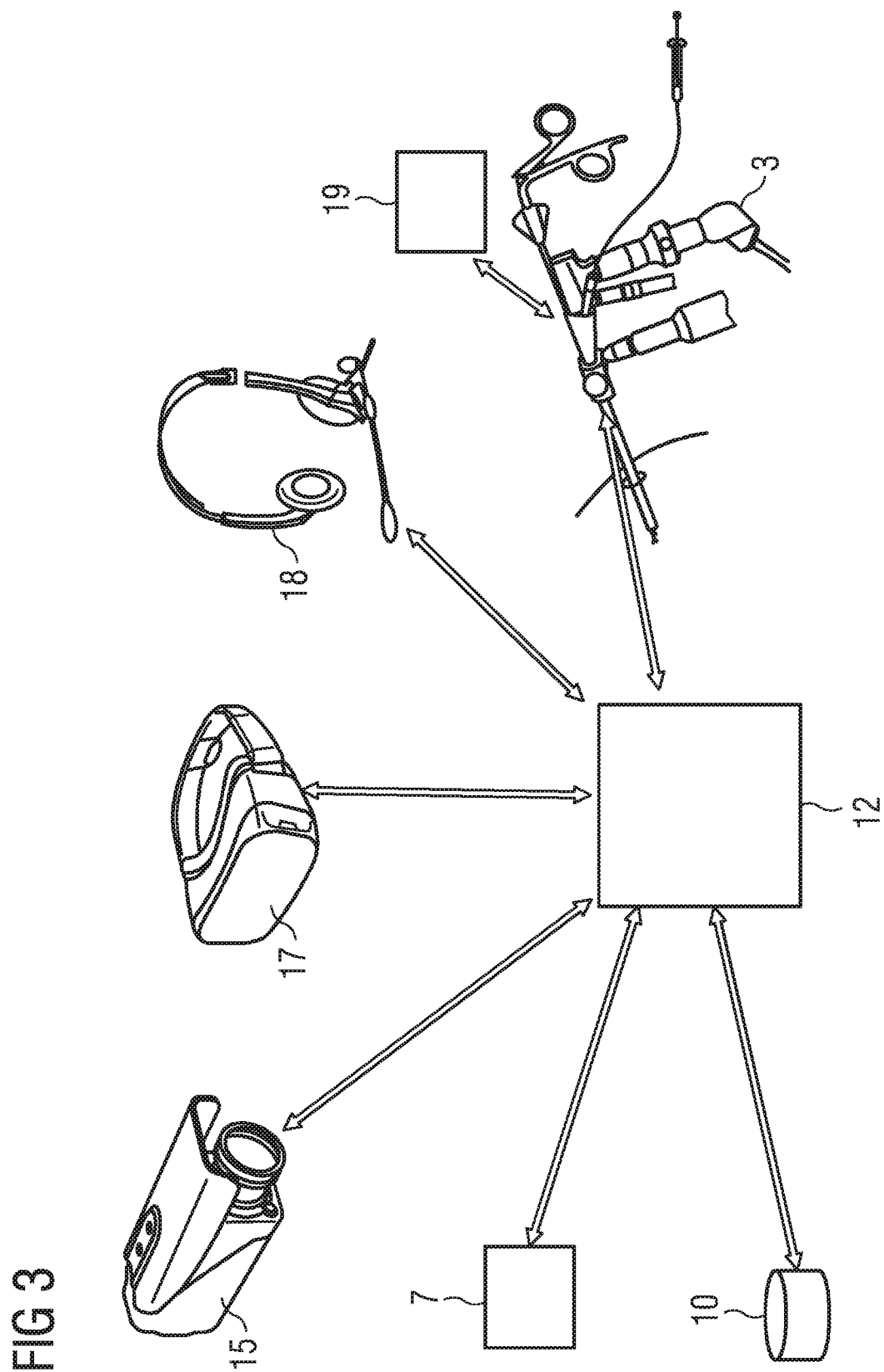
FIG. 3 shows a diagram of a preferred form of embodiment of an inventive image generation system together with provision and display components.

Different components that can interact with the image generation system 12 or that can be part of the image generation system 12, are shown once more schematically in FIG. 3. Double-ended arrows between the components are intended to represent the flow of data, which can run from the image generation system 12 to the components and from the components to the image generation system 12. The components are the aforementioned database 10, in which the information about the instrument image BIn is located, the computed tomograph 7, which delivers the image data for the structure image BS, a camera 15, which is needed for creation of the operation scene image BO, the AR headset 17, which displays the overlay image, control mechanisms 18, such as for example the headset, by which a control of the image generation system 12 with spoken commands is possible, and a medical instrument 3, which is equipped with forced feedback generators 19, such as e.g. vibrators, which can be activated by the image generation system 12 via the medical instrument 3 for warnings or a haptic feedback.

Figure 4:
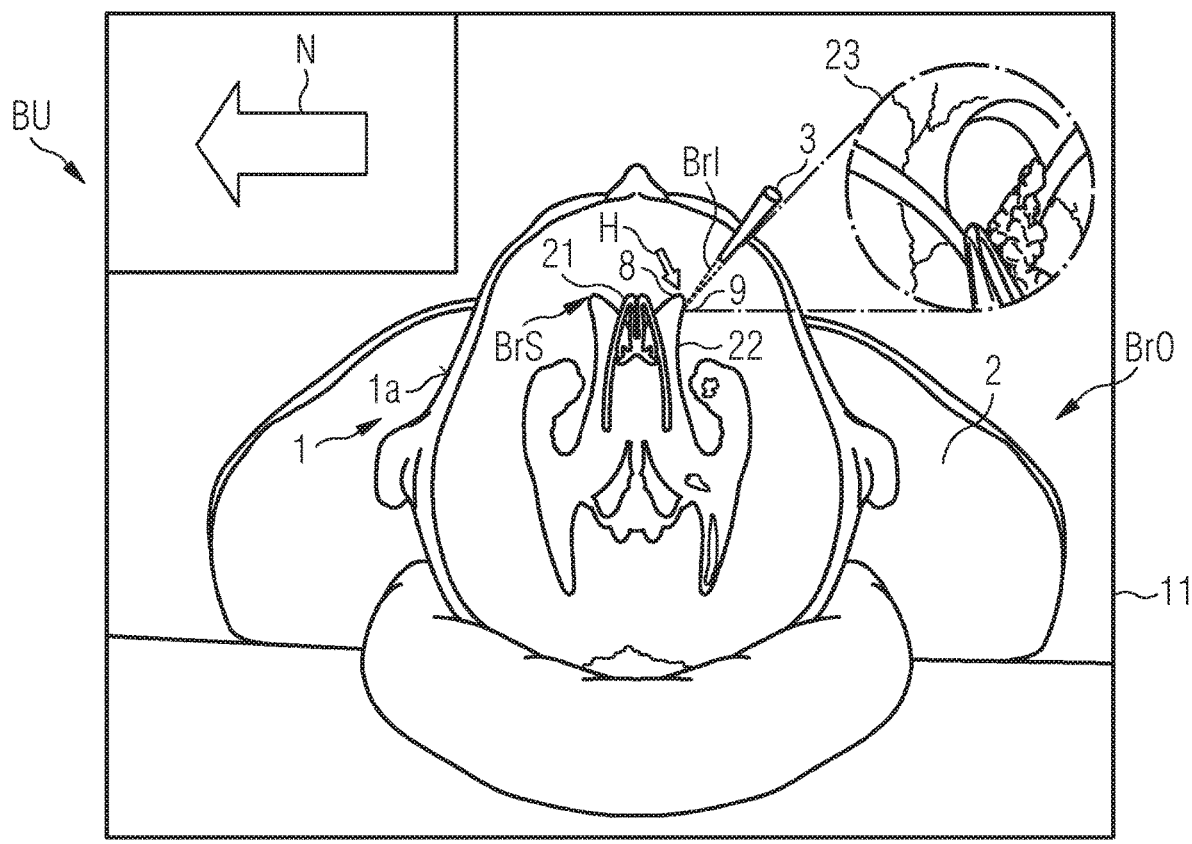
FIG. 4 shows a diagram of a preferred overlay image.

FIG. 4 shows a diagram of a preferred overlay image BU, as is generated for example by the image generation system 12 described previously and which could be displayed via the AR headset 17 in its field of view 11.

The basis for the overlay image BU is the registered operation scene image BrO, which shows the patient 2 as viewed by the operator 5 in FIG. 2 and which can also only be shown in part. Instead of the registered operation scene image BrO the real view of the patient 2 could also be shown, which is overlaid by the usual images within the framework of the augmented reality. It would also be possible, in the overlay image, for the operation scene to be shown partly real and partly in the form of the operation scene image. The operator 5, in a preferred form of embodiment, can also move around in the operating room, wherein the overlay image BU is preferably designed so that it always reproduces the field of view of the operator 5.

In reality the operator 5 only sees the patient 2, the area of the body 1, here the head 1, and indeed merely its surface 1a, and the medical element 3, however only the parts that have not penetrated into the head 1 of the patient 2. Other elements that are indicated in FIG. 4 will be supplemented by an embodiment of the inventive method. Thus the operator 5 now also sees the registered instrument image BrI of the part of the medical element 3 located in the head, in particular its tip 9, which can be additionally marked, e.g. via auxiliary information H, such as a small arrow. The auxiliary information could however also serve to make the destination structure 8 known, which could likewise be specially marked.

The entire internal structure of the head 1 of the patient 2 can be shown as a registered structure image BrS in the overlay image BU. In the present case the tip 9 of the medical element 3 has already almost reached the ventricle 22, and the outer parts of the brain have been hidden for a better view of the destination. Solely the ventricle 22 recognized automatically as object or destination structure 22 and a safety-relevant structure 21 of veins remains shown in the overlay image BU, so that the operator can find their way in the optimum manner.

Even if the tip 9 of the medical instrument 3 has apparently reached the destination structure 8 in the presentation, the image generation system recognizes that the tip 9 is located slightly too far to the right. Therefore navigation information N is shown in the upper left corner, which indicates that the operator 5 must move the tip 9 a little more to the left.

Also shown in the figure is the preferred case in which a live image 23 of an endoscope 3, i.e. an endoscope image 23, is available to the operator. In the case shown, it is shown as an enlargement of the region of the tip 9 in the upper right corner. It is however also possible, as described above, to display the endoscope image 23 directly in the region of the tip 9, in particular in the case of a zoom into the overlay image.

FIG. 5 shows a diagram of the execution sequence of a preferred form of embodiment of an inventive method. Shown schematically on the left-hand side are the structure image BS, the instrument image BIn and the operation scene image BO. The structure image BS is provided in step Ia to the image generation system 12 via its structure image interface 13, the instrument image BIn from the database 10 by the instrument image interface 14 and the operation scene image BO by the recording unit 15. The provision for the image generation system 12 means here that all three images will be processed in a registration step III by the registration unit 16, which creates a registered structure image BrS, a registered instrument image BrI and a registered operation scene image BrO. In practice the operation scene image BO will often be used as a reference image for the registration. In the event of the recording unit 15 being arranged in the AR headset, the operation scene image must still not actually be changed. Despite this, for reasons of clarity an unchanged image is also referred to as "registered", when the registration step III has been run through.

The registered images are overlaid as described to form an overlay image BU and sent to the AR headset 17 via the interface 20, wherein the overlaying step IV can take place as shown in the AR headset 17 or also in the image generation system, wherein the overlay image BU will be sent directly to the AR headset.

The method shown here using the example of setting up a ventricular drainage can be applied analogously for each instrument, which is introduced into the skull or other body cavities or organs (e.g. for biopsies).

Figure 6:
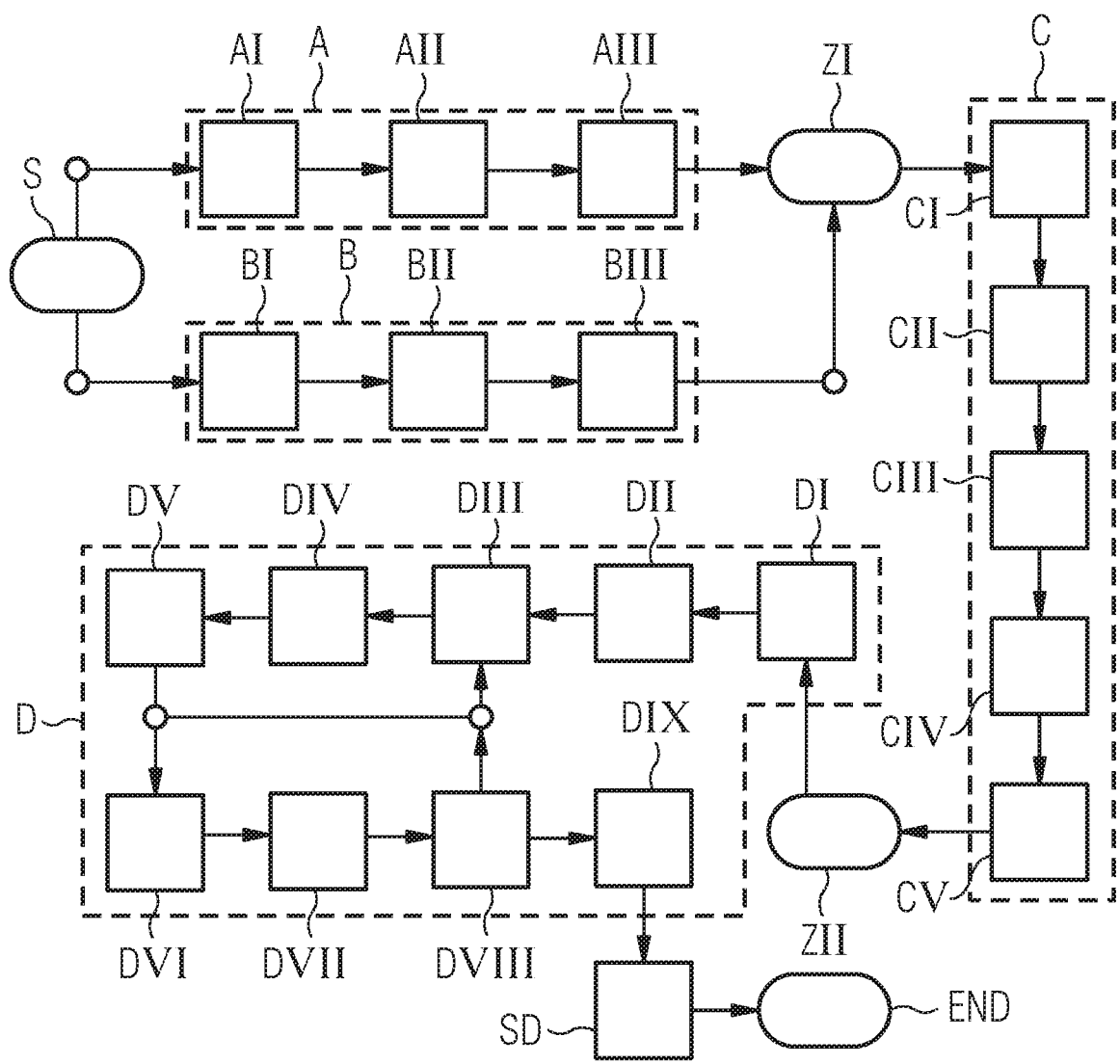
FIG. 6 shows a diagram of a flow diagram for the course of an example operation.

FIG. 6 shows a diagram of a flow diagram for the execution sequence of an example operation, wherein it is pointed out once again that the operation overall is not part of the invention, but only the imaging aspects. The Figure serves to this extent only to arrange an embodiment of the inventive steps in a context of a preferred use of the invention for support.

After a start procedure START, two routines A and B are run through, the results of which will be merged and processed in routine C. This passes its results to routine D, which forms the core of the method. After the routine D has ended there is a shutdown SD of the systems and the end of the execution sequence END.

In routine A, which serves to prepare the structure image BS, first of all, in step AI, the patient is irradiated in a computed tomograph, a magnetic resonance tomograph or another medical imaging device and in step AII a 3D reconstruction of the internal structures, in particular together with the outer contour, is generated. The inclusion of the outer contour has the advantage that later an assignment to the operation scene image becomes easier. In a last step AIII the recorded data is stored and is made available to routine C.

In routine B, which serves to prepare for the recording of the operation scene image BO or of a series of many operation scene images BO, first of all, in step BI, cameras are provided in the operation room or on the AR headset. This is followed, in step BII by a calibration of the image data in relation to the room, so that later a view of the patient 2 from each required angle of view can be created. The calibration matrix is made available in step BIII to the further method, so that later the registered operation scene image BrO can easily be created from the operation scene image BO.

In intermediate step ZI, first of all the data of the routines A and B is transferred to routine C, which serves for direct preparation. There, in step CI the cameras are started, in step CII the calibrations of the cameras are checked and in step CIII links between the data flows to the different input and output devices are established. Thereafter, in step CIV, a computation of the transformation matrix between two- and/or n three-dimensional mappings of the camera systems on the basis of anchor points is carried out and lastly, in step CV, the relationships between vectors is tested on the basis of simple tests, for example on the basis of standard vectors and their comparison in the other system in each case.

In intermediate step ZII the data of routine C is transferred to routine D.

While the routines A to C merely serve to prepare the images and the systems, the actual process, e.g. the imaging and registration, takes place in routine D. The patient 2 is positioned in step DI in the operating room and in step DII their position is calibrated or the system is calibrated to their position. Now, in steps DIII a DVIII a loop is executed, in order to validate the following of the medical instrument 3 in the patient 2 as often as possible. First of all, in step DIII, the patient 2 is localized, then, in step DIV, the localization of the area of the body, i.e. the location at which the operation is to take place, is sought in the room, then, in step DV, the contours of the structure image are registered with the real contours, e.g. with the scalp for a head operation, the medical instrument 3 is localized in step DVI and in step DVII the instrument image BIn is inserted into the overlay image. In a next step DVIII the action of the operator 5 is undertaken. Lastly, after completion of the operation, in step DIX, the patient 2 is brought out of the operating room again.

First and foremost a reduction of the complication rates is to be expected from the invention, since through the improved type of presentation itself, small structures can be reached in the first operation attempt. A further contribution is made by the optimum working posture of the surgeon, who via the invention can reach the structures "with their own eyes" so to speak.

A further advantage emerges from the automated creation of the overlay image and the optical registration of patient, instrument and structure image via cameras, in particular in the VR or AR display facility. Just with a recording of the operation scene image via cameras on the display facility it is to be expected that this is possible very much more quickly than carrying out the registration, during which cameras initially have to be set up in the room and aligned on the patient. Also a higher precision of the overlay image is expected, since the field of view of the operator and thus of the cameras is always aligned in the normal case on the reference points lying in the "Region of Interest" and thus no interference with other objects that are pushed into the field of view of the cameras can occur.

In conclusion it is pointed out once again that the method described in detail above as well as the system 12 presented merely involve example embodiments, which can be modified by the person skilled in the art in a wide diversity of ways, without departing from the area of the invention. Furthermore the use of the indefinite article "a" or "an" does not exclude the features concerned also being able to be present multiple times. Likewise the term "unit" and "module" does not exclude the components involved consisting of a number of interacting sub-components, which can possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for output of position information of a real medical instrument, the medical instrument being configured to at least partly penetrate an area of a real body of a patient, the method comprising:
   receiving a structure image including internal structures of the area of the body and receiving, from an instrument image database, an instrument image representing actual dimensions of the real medical instrument, including at least a part of the medical instrument used for an operation;
   creating a real operation scene image, including at least a surface of the area of the body and the real medical instrument;
   registering at least areas of the real operation scene image of the structure image with at least areas of the instrument image, wherein at least the structure image is registered with a corresponding area of the body in the real operation scene image and at least the instrument image is registered with the real medical instrument in the real operation scene image; and
   displaying an overlay image with a virtual reality (VR) or augmented reality (AR) display facility
   wherein at least one of
   the overlay image includes at least a part of the registered structure image in a form of an overlay with the registered real operation scene image or a real view of a corresponding part of a real area of the body and includes at least a part of the registered instrument image in the real area of the body, the real medical instrument being covered in the registered operation scene image by a surface of the area of the body, and the overlay image includes the operation scene image, the registered operation scene image and/or the real view of the corresponding part of the real area of the body together with a presentation of navigation data for the at least partial penetration of the real medical instrument at least partially penetrating the area of the body.

2. The method of claim 1, wherein the parts of the real medical instrument, visible in the operation scene image, are presented as a real map or as image data of the operation scene image in the overlay image.

3. The method of claim 1, wherein areas of the area of the body, through which the real medical instrument has already passed, are hidden in the presentation of the registered structure image or increased in transparency.

4. The method of claim 1, wherein for navigation based on the structure image, a destination structure of the at least partial penetration is established and at least one of a destination structure and a path to the destination structure in the overlay image is marked.

5. The method of claim 1, wherein at least one of
the real medical instrument includes a tip and a respective current position of the tip of the real medical instrument is marked automatically in the overlay image, and
wherein auxiliary information is incorporated into the overlay image, to make a destination structure in the body of the patient more easily reachable during the at least partial penetration.

6. The method of claim 1, wherein specific relevant structures of the area of the body are marked in the registered structure image, and wherein at least one of
the specific relevant structures are inserted color-coded by the display facility into the overlay image, and
possible collisions of the real medical instrument with the specific relevant structures are detected automatically.

7. The method of claim 4, wherein upon the destination structure or a position of the destination structure at least one of leaving a field of view of the display facility and coming back into the field of view of the display facility, the destination structure or a position of the destination structure is temporarily highlighted in the overlay image.

8. The method of claim 1, wherein at least one of
guidance of the real medical instrument is supported by forced feedback generators in a haptic way and
a haptic warning is issued when there is a threat of damage to specific internal structures of the area of the body.

9. The method of claim 1, wherein a deviation of a spatial course of the part of the real medical instrument located in the area of the body from a course is monitored and a warning signal is output upon the deviation exceeding a maximum permitted deviation.

10. The method of claim 1, wherein at least one of
parts of at least one of virtual mapping data and additional information is shown or hidden in the overlay image and
a function of devices is controlled via intelligent control mechanisms.

11. The method of claim 1, wherein the operation scene image is created from images recorded via cameras, and wherein the cameras concerned are at least one of integrated in the display facility and positioned in a room.

12. A non-transitory computer program product storing a computer program, directly loadable into a memory device of a display facility of a display system, including program sections for carrying out the method of claim 1, when the computer program is executed in the display facility of a display system.

13. A non-transitory computer-readable medium, storing program sections readable and executable by a computing unit, to carry out the method of claim 1 when the program sections are executed by the computing unit.

14. The method of claim 1, wherein for navigation based on the structure image, the destination structure of the at least partial penetration is established and at least one of the destination structure and a path to the registered structure image in the overlay is marked.

15. The method of claim 2, wherein areas of the area of the body, through which the real medical instrument has already passed, are hidden in the presentation of the registered structure image or increased in transparency.

16. The method of claim 2, wherein for navigation based on the structure image, the destination structure of the at least partial penetration is established and at least one of the destination structure and a path to the destination structure in the overlay image is marked.

17. The method of claim 2, wherein at least one of
the real medical instrument includes a tip and a respective current position of the tip of the real medical instrument is marked automatically in the overlay image, and
wherein auxiliary information is incorporated into the overlay image, to make the destination structure in the body of the patient more easily reachable during the at least partial penetration of the real medical instrument in the body of the patient.

18. The method of claim 1, wherein specific relevant structures of the area of the body are marked in the registered structure image.

19. The method of claim 6, wherein a warning signal is output upon possible collisions of the real medical instrument, with the specific relevant structures, being automatically detected.

20. The method of claim 5, wherein the destination structure or a position of the destination structure is marked temporarily in the overlay image, upon the destination structure or a position of the destination structure at least one of leaving the field of view of the display facility and coming back into a field of view of the display facility.

21. The method of claim 6, wherein the destination structure or a position of the destination structure is marked temporarily in the overlay image, upon the destination structure or a position of the destination structure at least one of leaving the field of view of the display facility and coming back into a field of view of the display facility.

22. The method of claim 1, wherein a live image of the operation scene is displayed along with the overlay image.

23. The method of claim 1, wherein the registered area of the instrument image is highlighted.

24. The method of claim 1, wherein specifically identified safety-relevant structures in the structure image cannot be hidden.

25. An image generation system for output of position information of a real medical instrument, the real medical instrument being configured to at least partly penetrate an area of a body of a patient, the image generation system comprising:
a camera configured to create an operation scene image including at least a surface of the area of the body and the real medical instrument;

memory storing computer-readable instructions;
one or more processors configured to execute the computer-readable instructions such that the one or more processors are configured to perform operations including,
  interfacing with a medical imaging system to receive a structure image including internal structures of the area of the body;
  interfacing with a database to receive an instrument image including at least a part of the real medical instrument;
  registering at least areas of the operation scene image, at least areas of the structure image and at least areas of the instrument image with one another, wherein at least the structure image and a corresponding area of the body are registered in the operation scene image and at least the instrument image is registered with the real medical instrument in the operation scene image; and
an interface for a virtual reality (VR) or augmented reality (AR) display facility, embodied to display an overlay image, wherein at least one of
  the overlay image includes at least a part of the registered structure image in a form of an overlay with the registered operation scene image or a real view of a corresponding part of a real area of the body and includes at least one part of the registered instrument image in the real area of the body, the real medical instrument being hidden in the registered operation scene image by a surface of the area of the body,
and
  the overlay image includes the operation scene image, the registered operation scene image and/or the real view of the corresponding part of the real area of the body with a presentation of navigation data for the at least partial penetration of the real medical instrument in the area of the body.

26. The image generation system of claim 25, further comprising:
  forced feedback generators, embodied to at least one of
  support guidance of the real medical instrument in a haptic way and
  issue a haptic warning when there is a threat of damage to internal structures of the area of the body, wherein the forced feedback generators are arranged in the real medical instrument.

* * * * *